(12) United States Patent
Jonczyk et al.

(10) Patent No.: US 6,645,991 B1
(45) Date of Patent: Nov. 11, 2003

(54) $\alpha_V\beta_3$ INTEGRIN INHIBITORS

(75) Inventors: Alfred Jonczyk, Darmstadt (DE);
Oliver Schadt, Rodenbach (DE);
Simon Goodman, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/069,187

(22) PCT Filed: Aug. 4, 2000

(86) PCT No.: PCT/EP00/07590

§ 371 (c)(1),
(2), (4) Date: Jun. 21, 2002

(87) PCT Pub. No.: WO01/14337

PCT Pub. Date: Mar. 1, 2001

(30) Foreign Application Priority Data

Aug. 24, 1999 (DE) .......................................... 199 39 980

(51) Int. Cl.[7] ........................ C07D 213/74; A61K 31/44
(52) U.S. Cl. ........................ 514/352; 514/275; 514/393; 514/398; 544/316; 546/307; 546/312; 548/307.4; 548/328.5; 548/335.1; 548/335.5; 548/341.5
(58) Field of Search ................................. 546/307, 312; 514/352, 273, 393, 398; 544/316; 548/307.4, 328.5, 335.1, 341.5

(56) References Cited

U.S. PATENT DOCUMENTS 5,234,936 A * 8/1993 Primeau et al. ........ 514/266.23
5,654,322 A * 8/1997 Hirata et al. ................ 514/363

FOREIGN PATENT DOCUMENTS

| EP | 628559 | * 12/1994 | ......... C07D/487/04 |
|----|--------|-----------|----------------------|
| WO | WO 9724124 A | 7/1997 | |
| WO | WO 9736882 A | 10/1997 | |
| WO | WO 9945927 A | 9/1999 | |
| WO | WO 0056729 A | 9/2000 | |

* cited by examiner

*Primary Examiner*—Zinna Northington Davis
(74) *Attorney, Agent, or Firm*—Millen, White, Zelano, Branigan, P.C.

(57) ABSTRACT

The invention describes novel compounds of the formula I which are biologically active as ligands of integrin $\alpha_V\beta_3$

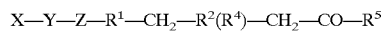

in which X, Y, Z, $R^1$, $R^2$, $R^4$ and $R^5$ are as defined in claim 1, and their physiologically acceptable salts and solvates.

16 Claims, No Drawings

$\alpha_v\beta_3$ INTEGRIN INHIBITORS

CROSS-REFERENCE TO RELATED APPLICATIONS

This application claims benefit of PCT/EP00/07590, filed Aug. 4, 2000, under 35 U.S.C. §371.

The invention relates to novel compounds of the formula I

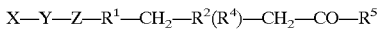

in which
X is $H_2N$—C(=NH)—, $H_2N$—C(=NH)—NH—, A—C(=NH)—NH—, $Het^1$— or $Het^1$—NH—, where the primary amino groups may also be provided with conventional amino-protecting groups,
Y is —$(CH_2)_n$—,

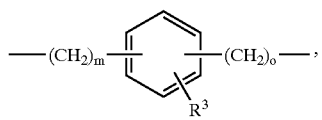

in which one, two, three or four methylene groups may be replaced by N, O and/or S,
Z is absent, —O—, —NH—, —NA—, —CH(OH)—, —CH(OA)—, —CHA—, —$CA_2$— or —S—,
$R^1$ is phenylene which is unsubstituted or mono-, di- or trisubstituted by F, Cl, Br, A, OA, $OCF_3$ or CN,
$R^2$ is N, CH or CA,
$R^3$ is H, F, Cl, Br, A, OA or $OCF_3$,
$R^4$ is phenyl, naphthyl or $Het^2$, each of which is unsubstituted or mono- or polysubstituted by A, aryl or $CF_3$,
$R^5$ is OH, OA, $NH_2$, NHA or $NA_2$,
$Het^1$ is a mono- or bicyclic heterocyclic radical having from 1 to 4 N atoms, which may be unsubstituted or mono- or disubstituted by $NH_2$,
$Het^2$ is an aromatic mono- or bicyclic heterocyclic radical having from 1 to 3 N, O and/or S atoms, which may be unsubstituted or mono- or disubstituted by F, Cl, Br, A, OA, SA, $OCF_3$, —CO—A, CN, COOA, $CONH_2$, CONHA, $CONA_2$ or $NO_2$,
aryl is phenyl which is unsubstituted or mono-, di- or trisubstituted by Hal, A or OA,
A is alkyl having 1–12 carbon atoms,
n is 1, 2, 3, 4, 5, 6, 7, 8, 9, 10, 11 or 12,
m, o are each, independently of one another, 0, 1, 2, 3, 4, 5, 6, 7, 8, 9, 10, 11 or 12,
and their physiologically acceptable salts and solvates.

The invention had the object of finding novel compounds having valuable properties, in particular those which can be used for the preparation of medicaments.

It has been found that the compounds of the formula I and their salts have very valuable pharmacological properties and are well tolerated. In particular, they act as integrin inhibitors, inhibiting, in particular, the interactions of the $\alpha_v$ integrin receptors with ligands. The compounds exhibit particular efficacy in the case of integrins $\alpha_v\beta_3$ and $\alpha_v\beta_5$. The compounds are very particularly effective as adhesion receptor antagonists for the $\alpha_v\beta_3$ receptor.

This action can be demonstrated, for example, by the method described by J. W. Smith et al. in J. Biol. Chem. 265, 11008–11013 and 12267–12271 (1990).

Inhibition of vitronectin binding to the receptor $\alpha_v\beta_3$ has been demonstrated experimentally for 3-phenyl-4-{4-[3-(pyridin-2-ylamino)propoxy]phenyl}-butyric acid.

B. Felding-Habermann and D. A. Cheresh in Curr. Opin. Cell. Biol. 5, 864 (1993), describe the importance of the integrins as adhesion receptors for a wide variety of phenomena and syndromes, especially in relation to the receptor $\alpha_v\beta_3$.

Other inhibitors of integrin $\alpha_v\beta_3$ are described in EP 0820988. The compounds according to the invention should be regarded as an invention of selection in relation to the said application. Vitronectin receptor antagonists are also described in WO 97/24124 and in EP 0820991.

The dependence of the occurrence of angiogenesis on the interaction between vascular integrins and extracellular matrix proteins has been described by P. C. Brooks, R. A. Clark and D. A. Cheresh in Science 264, 569–71 (1994).

The possibility of inhibiting this interaction and thus initiating apoptosis (programmed cell death) of angiogenic vascular cells by a cyclic peptide has been described by P. C. Brooks, A. M. Montgomery, M. Rosenfeld, R. A. Reisfeld, T.-Hu, G. Klier and D. A. Cheresh in Cell 79, 1157–64 (1994).

The experimental evidence that the compounds according to the invention also prevent the adhesion of living cells to the corresponding matrix proteins and accordingly also prevent the adhesion of tumour cells to matrix proteins can be provided in a cell adhesion test carried out analogously to the method of F. Mitjans et al., J. Cell Science 108, 2825–2838 (1995).

P. C. Brooks et al. in J. Clin. Invest. 96, 1815–1822 (1995) describe $\alpha_v\beta_3$ antagonists for combating cancer and for the treatment of tumour-induced angiogenic diseases.

The compounds of the formula I according to the invention can therefore be employed as medicament active ingredients, in particular for the treatment of tumour diseases, osteoporosis and other osteolytic diseases, and for the suppression of angiogenesis.

Compounds of the formula I which block the interaction of integrin receptors and ligands, such as, for example, of fibrinogen with the fibrinogen receptor (glycoprotein IIb/IIIa), prevent, as GPIIb/IIIa antagonists, the spread of tumour cells by metastasis. This is confirmed by the following observations:

The spread of tumour cells from a local tumour into the vascular system takes place through the formation of microaggregates (microthrombi) through interaction of the tumour cells with blood platelets. The tumour cells are screened by the protection in the microaggregate and are not recognised by the cells of the immune system.

The microaggregates are able to attach themselves to vessel walls, facilitating further penetration of tumour cells into the tissue. Since the formation of the microthrombi is promoted by fibrinogen binding to the fibrinogen receptors on activated blood platelets, the GPIIb/IIIa antagonists can be regarded as effective metastasis inhibitors.

Besides the binding of fibrinogen, fibronectin and Willebrand factor to the fibrinogen receptor of the blood platelets, compounds of the formula I also inhibit the binding of further adhesive proteins, such as vitronectin, collagen and laminin, to the corresponding receptors on the surface of various cell types. In particular, they prevent the formation of blood platelet thrombi and can therefore be employed for the treatment of thromboses, apoplexia, cardiac infarction, inflammation and arteriosclerosis.

The properties of the compounds can also be demonstrated by methods described in EP-A1-0 462 960. The inhibition of fibrinogen binding to the fibrinogen receptor can be demonstrated by the method indicated in EP-A1-0 381 033.

The thrombocyte aggregation-inhibiting action can be demonstrated in vitro by the method of Born (Nature 4832, 927–929, 1962). The inhibition of bone resorption by the compounds according to the invention can take place with the aid of an osteoclast resorption test analogously to WO 95/32710.

The invention accordingly relates to compounds of the formula I according to claim 1 and/or their physiologically acceptable salts for the preparation of a medicament for use as integrin inhibitor. In particular, the invention relates to compounds of the formula I according to claim 1 and/or their acceptable salts for the preparation of a medicament for combating pathologically angiogenic diseases, tumours, osteoporosis, inflammation and infections.

The compounds of the formula I can be employed as medicament active ingredients in human and veterinary medicine, for the prophylaxis and/or therapy of thromboses, myocardial infarction, arteriosclerosis, inflammation, apoplexia, angina pectoris, tumour diseases, osteolytic diseases, such as osteoporosis, hypercalcaemia, pathologically angiogenic illnesses, such as, for example, inflammation, ophthalmological illnesses, diabetic retinopathy, macular degeneration, myopia, ocular histoplasmosis, rheumatic arthritis, osteoarthritis, rubeotic glaucoma, ulcerative colitis, Crohn's disease, atherosclerosis, psoriasis, restenosis after angioplasty, viral infections, bacterial infections, fungal infections, in acute renal failure and in wound healing for supporting the healing processes.

The compounds of the formula I can be employed as antimicrobially active substances in operations where biomaterials, implants, catheters or cardiac pacemakers are used. They have an antiseptic action here. The effectiveness of the antimicrobial activity can be demonstrated by the method described by P. Valentin-Weigund et al. in Infection and Immunity, 2851–2855 (1988).

The invention also relates to the hydrates and solvates, for example alcoholates, of these compounds.

The invention furthermore relates to a process for the preparation of compounds of the formula I according to claim 1 and their salts, characterised in that
  a) a compound of the formula I is liberated from one of its functional derivatives by treatment with a solvolysing, reducing or hydrogenolysing agent, or
  b) a radical X and/or $R^5$ is converted into another radical X and/or $R^5$ by, for example,
    i) converting an amino group into a guanidino group by reaction with an amidinating agent,
    ii) saponifying an ester,
    iii) converting a hydroxyamidine into an amidine by hydrogenation,
and/or a base or acid of the formula I is converted into one of its salts.

The compounds of the formula I may have a chiral centre and may therefore occur in a plurality of stereoisomeric forms. All these forms (for example D and L forms) and mixtures thereof (for example the DL forms) are included in the formula I.

The compounds according to the invention also include so-called prodrug derivatives, i.e. compounds of the formula I which have been modified with, for example, alkyl or acyl groups, sugars or oligopeptides and which are rapidly cleaved in the organism to give the active compounds according to the invention.

The abbreviations mentioned above and below have the following meanings:

| | |
|---|---|
| Ac | acetyl |
| BOC | tert-butoxycarbonyl |
| CBZ or Z | benzyloxycarbonyl |
| DCCI | dicyclohexylcarbodiimide |
| DMF | dimethylformamide |
| EDCI | N-ethyl-N,N'-(dimethylaminopropyl)carbodiimide |
| Et | ethyl |
| Fmoc | 9-fluorenylmethoxycarbonyl |
| HOBt | 1-hydroxybenzotriazole |
| Me | methyl |
| Mtr | 4-methoxy-2,3,6-trimethylphenylsulfonyl |
| HONSu | N-hydroxysuccinimide |
| OBut | tert-butyl ester |
| Oct | octanoyl |
| OMe | methyl ester |
| OEt | ethyl ester |
| POA | phenoxyacetyl |
| TFA | trifluoroacetic acid |
| Trt | trityl (triphenylmethyl). |

Throughout the invention, all radicals which occur more than once, such as, for example, A, may be identical or different, i.e. are independent of one another.

A is alkyl and has 1, 2, 3, 4, 5, 6, 7 or 8 carbon atoms and is preferably methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyi, 1-ethyl-1-methylpropyl, 1-ethyl-2-methylpropyl, 1,1,2- or 1,2,2-trimethylpropyl, heptyl, octyl, nonyl, decyl, undecyl or dodecyl. Hydrogen atoms in the alkyl radicals may also be substituted by halogen atoms. A is therefore alternatively, for example, $CF_3$.

X is preferably, for example, pyrimidin-2-ylamino, pyridin-2-ylamino, imidazol-1-yl, imidazol-2-ylamino, benzimidazol-2-ylamino, 4,5-dihydroimidazol-2-ylamino, 2-aminoimidazol-5-ylamino, 2-aminopyridin-6-ylamino, 2-aminoimidazol-5-yl or 2-aminopyridin-6-yl.

Y is preferably, for example, ethylene, propylene or butylene.

Z is preferably, for example, O.

$R^1$ is preferably, for example, 1,4-phenylene.

$R^2$ is preferably, for example, CH or N, very particularly preferably CH.

$R^4$ is preferably, for example, phenyl.

$R^5$ is preferably, for example, OH.

$Het^1$ is preferably 1-, 2- or 3-pyrrolyl, 1-, 2-, 4- or 5-imidazolyl, 1-, 3-, 4- or 5-pyrazolyl, 2-, 3- or 4-pyridyl, 2-, 4-, 5- or 6-pyrimidinyl, each of which is unsubstituted or mono- or disubstituted by A, NHA and/or $NH_2$, furthermore preferably 1,2,3-triazol-1-, -4- or-5-yl, 1,2,4-triazol-1-, -3- or 5-yl, 1- or 5-tetrazolyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 3-, 4-, 5-, 6-, 7- or 8-quinolyl, 1-, 3-, 4-, 5-, 6-, 7- or 8-isoquinolyl, 7- or 8-cinnolyl, 2-, 4-, 5-, 6-, 7- or 8-quinazolinyl, 1H-imidazo [4,5-b]pyridin-2-yl or 1,8-naphthyridin-7-yl.

The heterocyclic radicals may also be partially or fully hydrogenated. $Het^1$ may thus, for example, also be 2,3-dihydro-1-, -2-, -3-, -4- or -5-pyrrolyl, 2,5-dihydro-1-, -2-, -3-, 4- or -5-pyrrolyl, 1-, 2- or 3-pyrrolidinyl, tetrahydro-1-, -2- or -4-imidazolyl, 4,5-dihydroimidazol-2-yl, 2,3-dihydro-1-, -2-, -3-, 4- or -5-pyrazolyl, tetrahydro-1-, -3- or -4-pyrazolyl, 1,4-dihydro-1-, -2-, -3- or -4-pyridyl, 1,2,3,4- tetrahydro-1-, -2-, -3-, 4-, -5- or -6-pyridyl, 1-, 2-, 3- or 4-piperidinyl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-,-7- or -8-isoquinolyl or 1,2,3,4-tetrahydro-1,8-naphthyridin-7-yl.

Hydrogenated or partially hydrogenated Het¹ radicals may additionally be substituted by =NH or carbonyloxygen.

Het² is preferably 2,3-, 2,4-, 2,5- or 3,4-thienyl, 2,3-, 2,4-, 2,5- or 3,4-pyrrolyl, 2,4-, 2,5- or 4,5-imidazolyl, 2,3-, 2,4-, 2,6- or 3,5-pyridyl, 2,4-, 2,5-, 2,6-, 4,5- or 5,6-pyrimidinyl, each of which is unsubstituted or mono-substituted by F, Cl, Br, A, OA or OCF₃.

n is preferably 2, 3, 4, 5 or 6. furthermore also 1, 7 or 8; n is very particularly preferably 3, 4 or 5.

m and o are preferably, each independently of one another, 0, 1 or 2, they are very particularly preferably 0.

Amino-protecting group is preferably formyl, acetyl, propionyl, butyryl, phenylacetyl, benzoyl, tolyl, POA, methoxycarbonyl, ethoxycarbonyl, 2,2,2-trichloroethoxycarbonyl, BOC, 2-iodoethoxycarbonyl, CBZ ("carbobenzoxy"), 4-methoxybenzyloxycarbonyl, FMOC, Mtr or benzyl.

Accordingly, the invention relates, in particular, to the compounds of the formula I in which at least one of the radicals mentioned has one of the preferred meanings indicated above. Some preferred groups of compounds can be expressed by the following sub-formulae Ia to Ii, which conform to the formula I and in which the radicals not denoted in greater detail have the meaning indicated under the formula I, but in which

| | | |
|---|---|---|
| in a) | X | is pyrimidin-2-ylamino, pyridin-2-ylamino, imidazol-1-yl, imidazol-2-ylamino, benzimidazol-2-ylamino, 4,5-dihydroimidazol-2-ylamino, 2-aminoimidazol-5-ylamino, 2-aminopyridin-6-ylamino, 2-aminoimidazol-5-yl or 2-aminopyridin-6-yl; |
| in b) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3, or 4; |
| in c) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3 or 4; |
| in d) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3 or 4, |
| | Z | is O; |
| in e) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3 or 4, |
| | Z | is O, |
| | R² | is N or CH; |
| in f) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3 or 4, |
| | Z | is O, |
| | R² | is N or CH, |
| | R⁴ | is phenyl which is unsubstituted or substituted by A, aryl or CF₃; |
| in g) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3 or 4, |
| | Z | is O, |
| | R² | is N or CH, |
| | R⁴ | is phenyl which is unsubstituted or substituted by A, aryl or CF₃, |
| | R⁵ | is OA or OH; |
| in h) | X | is pyrimidin-2-ylamino, pyridin-2-ylamino, imidazol-1-yl, imidazol-2-ylamino, benzimidazol-2-ylamino, 4,5-dihydroimidazol-2-ylamino, 2-aminoimidazol-5-ylamino, 2-aminopyridin-6-ylamino, 2-aminoimidazol-5-yl or 2-aminopyridin-6-yl, |
| | Y | is —(CH₂)ₙ—, |
| | n | is 2, 3 or 4, |
| | Z | is O, |
| | R² | is N or CH, |
| | R⁴ | is unsubstituted phenyl, |
| | R⁵ | is OA or OH; |
| in i) | X | is pyrimidin-2-ylamino, pyridin-2-ylamino, imidazol-1-yl, imidazol-2-ylamino, benzimidazol-2-ylamino or 4,5-dihydroimidazol-2-ylamino, |
| | Y | is —(CH₂)ₙ—, |
| | n | is 2, 3 or 4, |
| | Z | is O, |
| | R² | is N or CH, |
| | R⁴ | is unsubstituted phenyl, |
| | R⁵ | is OA or OH; |

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

Compounds of the formula I can preferably be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'-N group, in which R' is an amino-protecting group, instead of an HN group, and/or those which carry a hydroxyl-protecting group instead of the H atom of a hydroxyl group, for example those which conform to the formula I, but carry a —COOR" group, in which R" is a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1–20, in particular 1–8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as formyl, acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkyloxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl, formyl and acetyl.

The amino-protecting group is cleaved off—depending on the protecting group used—for example using strong acids, advantageously using. TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent and/or small amounts of a scavenger, such as water, a phenol or a thiol, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane, TFA containing approximately 3% of water or using approximately 3 to 5N HCl in dioxane at 15–30°, and the FMOC group can be cleaved off using an approximately 5 to 50% solution of sec-amines, such as dimethylamine, diethylamine or piperidine, in DMF at 15–30°.

Protecting groups which can be removed hydrogenolytically (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20–30° and 1–10 bar. Hydrogenolysis of the CBZ group succeeds well, for example, on 5 to 10% Pd/C in methanol or using ammonium formate (instead of hydrogen) on Pd/C in methanol/DMF at 20–30°.

Examples of suitable inert, solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, water, or mixtures of the said solvents.

It is furthermore possible to saponify an ester of the formula I. This is advantageously carried out by solvolysis or hydrogenolysis, as indicated above, for example using LiOH in methanol, NaOH or KOH in dioxane/water, at temperatures between 0 and 60° C., preferably between 10 and 40° C.

The conversion of a cyano group into an amidino group is carried out by reaction using, for example, hydroxylamine followed by reduction of the N-hydroxyamidine with hydrogen in the presence of a catalyst, such as, for example, Pd/C.

It is furthermore possible to replace a conventional amino-protecting group by hydrogen by cleaving off the protecting group, as described above, solvolytically or hydrogenolytically or by liberating an amino group protected by a conventional protecting group by solvolysis or hydrogenolysis. In order to prepare compounds of the formula I in which X is H$_2$N—C(=NH)—NH—, a corresponding amino compound can be treated with an amidinating agent. The preferred amidinating agent is 1-amidino-3,5-dimethylpyrazole (DPFN), which is employed, in particular, in the form of its nitrate. The treatment is advantageously carried out with addition of a base, such as triethylamine or ethyldiisopropylamine, in an inert solvent or solvent mixture, for example water/dioxane, at temperatures between 0 and 120° C., preferably between 60 and 120° C.

In order to prepare an amidine of the formula I (X=–c (=NH)—NH$_2$), ammonia can be adducted onto a nitrile of the formula I (X=CN). The adduction is preferably carried out in a number of steps by, in a manner known per se, a) converting the nitrile using H$_2$S into a thioamide, which is converted using an alkylating agent, for example CH$_3$I, into the corresponding S-alkylimidothioester, which itself reacts with NH$_3$ to give the amidine, b) converting the nitrile using an alcohol, for example ethanol, in the presence of HCl into the corresponding imidoester, and treating this with ammonia, or c) reacting the nitrile with lithium bis(trimethylsilyl)amide; and subsequently hydrolysing the product.

Preference is furthermore given to the liberation of the compounds of the formula I from an oxidised precursor by, for example, reducing an oxyheterocyclic compound using a reducing agent, such as, for example, phosphorus trichloride, in an inert solvent.

Free amino groups can furthermore be acylated in a conventional manner using an acid chloride or anhydride or alkylated using an unsubstituted or substituted alkyl halide, advantageously in an inert solvent, such as dichloromethane or THF and/or in the presence of a base, such as triethylamine or pyridine, at temperatures between –60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfonic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, an acid of the formula I can be converted into one of its physiologically acceptable metal or ammonium salts by reaction with a base. Possible salts here are, in particular, the sodium, potassium, magnesium, calcium and ammonium salts, furthermore substituted ammonium salts, for example the dimethyl-, diethyl- or diisopropylammonium salts, monoethanol-, diethanol- or diisopropylammonium salts, cyclohexyl- or dicyclohexylammonium salts, dibenzylethylenediammonium salts, furthermore, for example, salts with arginine or lysine.

The compounds of the formula I contain one or more chiral centres and can therefore exist in racemic or optically active form. The racemates obtained can be resolved into the enantiomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture, for example in the volume ratio 82:15:3.

It is of course also possible to obtain optically active compounds of the formula I by the methods described above by using starting materials which are already optically active.

The invention covers not only the said compounds, but also mixtures and preparations which, besides these compounds according to the invention, also comprise other pharmacological active ingredients or adjuvants which are able to influence the primary pharmacological action of the compounds according to the invention in the desired manner. These may be used as therapeutic agents, diagnostic agents or as reagents. They can be administered to humans or animals locally or systemically, orally, intravenously, intraperitoneally, intramuscularly, subcutaneously, transdermally, nasally, buccally or iontophoretically, including formulations in suspensions, emulsions or solutions, liposomes, ointments, pastes, biodegradable polymers or as nanoparticles, tablets, capsules or pills, granules or powders, as an aerosol for inhalation, as intranasal drops or sprays. A combination of the novel products with other techniques, such as surgery, irradiation, diagnosis, radiotherapy, photodynamic therapy and gene therapy, and with other medicaments is also possible. Such medicaments may originate, for example, from the areas of the cardiovascular system, central nervous system or oncology. They may be tumour agents, such as angiogenesis inhibitors or cytostatics, chemotherapeutic agents from the group consisting of alkylating agents, antibiotics, antimetabolites, biological agents and immunomodulators, hormones and antagonists thereof, mustard gas derivatives, alkaloids and others, it being possible for these substances to be of low molecular weight and high molecular weight. They may be lipids, carbohydrates or proteins. Also included are cytokines, toxins, fusion proteins, monoclonal antibodies and vaccines.

The invention accordingly relates to compounds of the formulae defined above and below and in the claims, including their physiologically acceptable salts, as medicaments, diagnostic agents or reagents.

The invention relates in particular to corresponding medicaments as inhibitors for combating illnesses based indirectly or directly on expression of the $\alpha_v\beta_3$ integrin receptor, i.e. in particular in pathologically angiogenic illnesses, thromboses, cardiac infarction, coronary heart diseases, arteriosclerosis, tumours, osteoporosis, inflammation, infections and for influencing wound-healing processes.

The invention also relates to corresponding pharmaceutical preparations which comprise at least one medicament of the formula I and, if desired, excipients and/or assistants.

The invention furthermore relates to the use of the compounds and/or their physiologically acceptable salts according to the claims and description for the preparation of a medicament for combating illnesses based indirectly or directly on expression of the $\alpha_v\beta_3$ integrin receptor, i.e. in particular in pathologically angiogenic illnesses, thromboses, cardiac infarction, coronary heart diseases, arteriosclerosis, tumours, osteoporosis, inflammation, infections and for influencing wound-healing processes. The medicaments according to the invention or the pharmaceutical preparations comprising them can be used in human or veterinary medicine. Suitable excipients are organic or inorganic substances which are suitable for enteral (for example oral) or parenteral administration or topical application or for administration in the form of an inhalation spray and which do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds can also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins. For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronised form, in which case one or more additional physiologically acceptable solvents may be present, for example ethanol. Inhalation solutions can be administered with the aid of conventional inhalers.

The substances according to the invention can generally be administered analogously to other known commercially available preparations (for example described in U.S. Pat. No. 4,472,305), preferably in doses of between about 0.05 and 500 mg, in particular between 0.5 and 100 mg, per dosage unit. The daily dose is preferably between about 0.01 and 20 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular illness to which the therapy applies. Parenteral administration is preferred. Above and below, all temperatures are given in ° C.

The HPLC analyses (retention time Rt) were carried out in the following system:

3 μm Silica Rod column with a 210 second gradient from 20 to 100% water/acetonitrile/0.01% of trifluoroacetic acid, at a flow rate of 2.2 ml/min and detection at 220 nm.

Mass spectrometry (MS):
EI (electron impact ionisation) M+
FAB (fast atom bombardment) (M+H)+

EXAMPLE 1

Synthesis of 3-Phenyl-4-{4-[3-(pyridin-2-ylamino) propoxy]phenyl}butyric Acid 835 mg of Mg are suspended in 5 ml of abs. THF. A solution of 2.0 g of 4-benzyloxybenzyl chloride in 5 ml of abs. tetrahydrofuran is subsequently added dropwise. When the addition is complete, the cloudy solution is stirred at room temperature for a further 1 hour, a solution of 1.73 g of ethyl 2-cyano-3-phenylacrylate in 10 ml of abs. toluene is subsequently added, and the mixture is refluxed for 16 hours. The solvent is removed, and conventional work-up gives ethyl 4-(4-benzyloxyphenyl)-2-cyano-3-phenylbutyrate ("AA").

8.27 g of "AA" are suspended in a mixture of 80 ml of acetic acid and 80 ml of conc. HCl and subsequently refluxed for 16 hours. Conventional work-up gives 4-(4-hydroxyphenyl)-3-phenylbutyric acid ("AB").

0.4 ml of thionyl chloride is added to a solution of 1.0 g of "AB" in 10 ml of abs. methanol, and the mixture is stirred at room temperature for 16 hours. Conventional work-up gives methyl 4-(4-hydroxyphenyl)-3-phenylbutyrate ("AC").

0.62 ml of diethyl azadicarboxylate is added dropwise to a suspension of 0.4 g of "AC", 0.5 g of 3-(1-oxypyridin-2-ylamino)propan-1-ol and 1.23 g of polymer-bound triphenylphosphine (loading about 3 mmol/g) in 17 ml of abs. THF, and the mixture is stirred for a further 16 hours. After filtration and removal of the solvent, the product is purified by HPLC, giving methyl 3-phenyl-4-{4-[3-(1-oxypyridin-2-ylamino)propoxy]phenyl}butyrate ("AD").

0.59 g of phosphorus trichloride is added to a solution of 0.45 g of "AD" in 30 ml of chloroform, and the mixture is stirred for 2 hours at room temperature and for a further 2 hours under reflux. After conventional work-up, 0.2 g of lithium hydroxide is added to the residue in 15 ml of methanol, and the mixture is stirred at room temperature for 16 hours. After removal of the solvent, 0.66 ml of trifluoroacetic acid is added, and the product is purified by HPLC, giving 3-phenyl-4-{4-[3-(pyridin-2-ylamino)propoxy] phenyl}butyric acid, trifluoroacetate, Rt 1.209, FAB 391.1

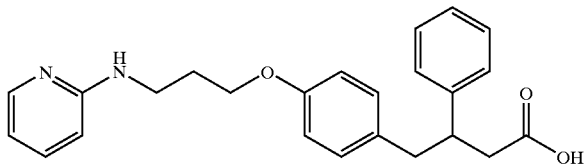

Test Result of $\alpha_v\beta_3$ Inhibition by 3-Phenyl-4-{4-[3-(pyridin-2-ylamino)-propoxy]phenyl}butyric Acid For the vitronectin binding test, the $IC_{50}$ value is given, i.e. the concentration in nmol/litre which inhibits 50% of the vitronectin binding to the corresponding isolated receptor (method of Smith et al., J. Biol. Chem. 265, 12267–71, 1990).

$IC_{50}\alpha_v\beta_3$: 5.3.

The pharmacological data confirm the antagonistic activity of the compound according to the invention for the receptor $\alpha_v\beta_3$.

The following compounds are obtained analogously to the synthetic scheme described above 3-phenyl-4-{4-[2-(pyrimidin-2-ylamino)ethoxy] phenyl}butyric acid, trifluoroacetate, Rt 1.680, FAB 377.9;

3-phenyl-4-{4-[3-(pyrimidin-2-ylamino)propoxy] phenyl}butyric acid, trifluoroacetate, Rt 1.701, FAB 391.6;

3-phenyl-4-{4-[4-(pyrimidin-2-ylamino)butoxy] phenyl}butyric acid, trifluoroacetate, Rt 1.751, FAB 406.0;

3-phenyl-4-{4-[2-(pyridin-2-ylamino)ethoxy] phenyl}butyric acid, trifluoroacetate, Rt 1.144, FAB 377.1;

3-phenyl-4-{4-[4-(pyridin-2-ylamino)butoxy] phenyl}butyric acid, trifluoroacetate, Rt 1.248, FAB 405.2;

3-phenyl-4-{4-[3-(imidazol-1-yl)propoxy] phenyl}butyric acid;

3-phenyl-4-{4-[3-(4,5-dihydro-1H-imidazol-2-ylamino) propoxy]phenyl}-butyric acid;

3-phenyl-4-{4-[3-(imidazol-2-ylamino)propoxy] phenyl}butyric acid;

3-phenyl-4-{4-[3-(benzimidazol-2-ylamino)propoxy] phenyl}butyric acid;

3-phenyl-4-{4-[3-(2-aminopyridin-6-ylamino)propoxy] phenyl}butyric acid, 3-phenyl-4-{4-[3-(2-aminoimidazol-5-ylamino)propoxy] phenyl}butyric acid.

EXAMPLE 2

Synthesis of (Phenyl{4-[3-(pyridin-2-ylamino) propoxy]benzyl}amino)acetic Acid 40.0 g of 4-hydroxybenzaldehyde are dissolved in 400 ml of abs. THF under a protective-gas atmosphere, 55.1 g of dihydropyran and 13.7 g of pyridinium p-toluenesulfonate are added, and the mixture is stirred overnight at room temperature. The solvent is removed in a rotary evaporator, and the residue is subjected to conventional work-up, giving 4-(tetrahydropyran-2-yloxy)benzaldehyde ("BA") as a colourless oil.

1.17 g of aniline are added to a solution of 2.0 g of "BA" in 20 ml of abs. methanol, and the mixture is stirred at 60° for 3 hours. 0.79 g of sodium cyanoborohydride are added at room temperature, and the reaction solution is refluxed for 16 hours. Removal of the solvent, conventional work-up and purification by chromatography gives phenyl[4-(tetrahydropyran-2-yloxy)benzyl]amine ("BB") as a colourless liquid.

8.0 g of "BB" and 10.36 g of methyl bromoacetate are dissolved in 100 ml of abs. THF under an $N_2$ atmosphere, 12.0 g of potassium carbonate are added, and the mixture is refluxed for 16 hours. Removal of the solvent, conventional work-up and purification by chromatography gives methyl {phenyl[4-(tetrahydropyran-2-yloxy)benzyl]amino}acetate ("BC") as a colourless solid.

2.76 ml of conc. HCl are added to a solution of 0.5 g of "BC" in 25 ml of methanol and 5 ml of dichloromethane, and the mixture is stirred at room temperature for 5 minutes. After removal of the solvent and conventional work-up, the residue is dissolved in 16 ml of abs. THF together with 0.47 g of 3-(1-oxypyridin-2-ylamino)propan-1-ol, and 1.17 g of polymeric triphenylphosphine (loading about 3 mmol/g) are subsequently added. 0.62 ml of diethyl azadicarboxylate are subsequently added dropwise. The suspension is then stirred at room temperature for 16 hours. After filtration and removal of the solvent, the product is purified by HPLC, giving methyl ({4-[3-(1-oxypyridin-2-ylamino)propoxy]benzyl}phenylamino)acetate ("BD").

0.57 g of phosphorus trichloride is added to a solution of 0.44 g of "BD" in 30 ml of chloroform, and the mixture is stirred for 2 hours at room temperature and for a further 2 hours under reflux. After conventional work-up, 0.27 g of lithium hydroxide is added to the residue in 15 ml of methanol, and the mixture is stirred at room temperature for 16 hours. After removal of the solvent, 0.66 ml of trifluoroacetic acid is added, and the product is purified by HPLC, giving (phenyl{4-[3-(pyridin-2-ylamino)propoxy]benzyl}-amino)acetic acid, bistrifluoroacetate

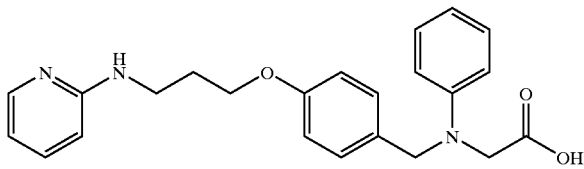

The following compounds are obtained analogously
(phenyl{4-[2-(pyrimidin-2-ylamino)ethoxy]benzyl}amino)acetic acid,
(phenyl{4-[3-(pyrimidin-2-ylamino)propoxy]benzyl}amino)acetic acid, Rt 1.517, FAB 392.8;
(phenyl{4-[4-(pyrimidin-2-ylamino)butoxy]benzyl}amino)acetic acid,
(phenyl{4-[2-(pyridin-2-ylamino)ethoxy]benzyl}amino)acetic acid,
(phenyl{4-[4-(pyridin-2-ylamino)butoxy]benzyl}amino)acetic acid, Rt 1.336, FAB 406.1;
(phenyl{4-[3-(imidazol-1-yl)propoxy]benzyl}amino)acetic acid,
(phenyl{4-[3-(4,5-dihydro-1H-imidazol-2-ylamino)propoxy]benzyl}amino)-acetic acid,
(phenyl{4-[3-(imidazol-2-ylamino)propoxy]benzyl}amino)acetic acid,
(phenyl{4-[3-(benzimidazol-2-ylamino)propoxy]benzyl}amino)acetic acid.

The examples below relate to pharmaceutical preparations:

EXAMPLE A

Injection Vials

A solution of 100 g of 3-phenyl-4-{4-[3-(pyridin-2-ylamino)propoxy]phenyl}-butyric acid and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of 3-phenyl-4-{4-[3-(pyridin-2-ylamino)propoxy]phenyl}-butyric acid with 100 g of soya lecithin and 1400 g of cocoa butter is melted, poured into moulds and allowed to cool. Each suppository contains 20 mg of active ingredient.

EXAMPLE C

Solution

A solution is prepared from 1 g of 3-phenyl-4-{4-[3-(pyridin-2-ylamino)-propoxy]phenyl}butyric acid, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of 3-phenyl-4-{4-[3-(pyridin-2-ylamino)propoxy]phenyl}butyric acid are mixed with 99.5 g of Vaseline under aseptic conditions.

EXAMPLE E

Tablets

A mixture of 1 kg of 3-phenyl-4-{4-[3-(pyridin-2-ylamino)propoxy]phenyl}-butyric acid, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of 3-phenyl-4-{4-[3-(pyridin-2-ylamino)propoxy]phenyl}butyric acid are introduced into hard gelatine capsules in a conventional manner in such a way that each capsule contains 20 mg of the active ingredient.

EXAMPLE H

Ampoules

A solution of 1 kg of 3-phenyl-4-{4-[3-(pyridin-2-ylamino)propoxy]phenyl}-butyric acid in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of 3-phenyl-4-{4-[3-(pyridin-2-ylamino)propoxy]phenyl}butyric acid are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

What is claimed is:

1. A compound of the formula I $$X—Y—Z—R^1—CH_2—R^2(R^4)—CH_2—CO—R^5$$

in which

X is $H_2N—C(=NH)—$, $H_2N—C(=NH)—NH—$, $A—C(=NH)—NH—$, $Het^1-$ or $Het^1-NH—$,
where the primary amino groups may also be provided with conventional amino-protecting groups, Y is

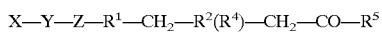

is —$(CH_2)_n$—, 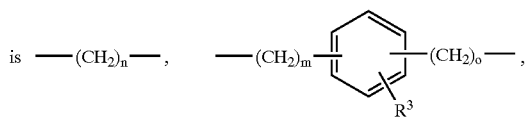

in which one, two, three or four methylene groups may be replaced by N, O and/or S, Z is —O—, —NH—, —NA—, —CH(OH)—, —CH(OA)—, —CHA, —CA$_2$—or —S—, $R^1$ is phenylene which is unsubstitued or mono-, di- or trisubstituted by F, Cl, Br, A, OA, OCF$_3$, or CN, $R^2$ is N, CH, or CA, $R^3$ is H, F, Cl, Br, A, OA or OCF$_3$, $R^4$ is phenyl, naphthyl or Het$^2$, each of which is unsubstituted or mono- or polysubstituted by A, aryl, or CF$_3$, $R^5$ is OH, OA, NH$_2$, NHA or NA$_2$, Het$^1$ is a mono- or bicylic heterocyclic radical having from 1 to 4 N atoms, which may be unsubstituted or mono- or disubstituted by NH$_2$, Het$^2$ is an aromatic mono- or bicylic heterocyclic radical having from 1 to 3 N, O and/or S atoms, which may be unsubstituted or mono- or disubstituted by F, Cl, Br, A, OA, SA, OCF$_3$, —CO—A, CN, COOA, CONH$_2$, CONHA, CONA$_2$, or NO$_2$, aryl is phenyl which is unsubstituted or mono-, di-, or trisubstituted by Hal, A or OA, A is alkyl having 1–12 carbon atoms, n is 1, 2, 3, 4, 5, 6, 7, 8, 9, 10, 11 or 12, m, o are each, independently of one another, 0, 1, 2, 3, 4, 5, 6, 7, 8, 9, 10, 11, or 12, or a physiologically acceptable salt or solvate thereof.

2. A compound according to claim 1, wherein said compound is:
 a) 3-phenyl-4-{4-[3-(pyridine-2-ylamino)propoxy]phenyl}butyric acid or a physiologically acceptable salt or solvate thereof;
 b) 3-phenyl-4-{4-[3-(2-aminopyridin-6-ylamino)propoxy]phenyl}-butyric acid or a physiologically acceptable salt or solvate thereof, or
 c) 3-phenyl-4-{4-[3-(2-aminoimidazol-5-ylamino)propoxy}-phenyl}butyric acid or a physiologically acceptable salt or solvate thereof.

3. A process for the preparation of a compound according to claim 1, said process comprising:
 a) a compound of the formula I is liberated from one of its functional derivative by treatment with a solvolysing, reducing or hydrogenolysing agent, or
 b) a radical X and/or R is converted into another radical X and/or $R^5$ by,
  i) converting an amino group into a guanidine group by reaction with an amidinating agent,
  ii) saponifying an ester,
  iii) converting a hydroxylamine into an amidine by hydrogenation, and/or a base or acid of the formula I is converted into one of its salts.

4. A compound according to claim 1, wherein X is pyrimidin-2-ylamino, pyridin-2-ylamino, imidazol-1-yl, imidazol-2-ylamino, benzimidazol-2-ylamino, 4,5-dihydroimidazol-2-ylamino, 2-aminoimidazol-5-ylamino, 2-aminopyridin-6-ylamino, 2-aminoimidazol-5-yl or 2-aminopyridin-6-yl.

5. A compound according to claim 1, wherein X is pyrimidin-2-ylamino, pyridin-2-ylamino, imidazol-1-yl, imidazol-2-ylamino, benzimidazol-2-ylamino or 4,5-dihydroimidazol-2-ylamino, Y is —$(CH_2)_n$—, and n is 2, 3, or 4.

6. A compound according to claim 1, wherein X is pyrimidin-2-ylamino, pyridin-2-ylamino, imidazol-1-yl, imidazol-2-ylamino, benzimidazol-2-ylamino or 4,5-dihydroimidazol-2-ylamino, Y is —$(CH_2)_n$—, n is 2, 3 or 4, and Z is O.

7. A compound according to claim 1, wherein is pyrimidin-2-ylamino, pyridin-2-ylamino, imidazol-1-yl, imidazol-2-ylamino, benzimidazol-2-ylamino or 4,5-dihydroimidazol-2-ylamino, Y is —$(CH_2)_n$—, n is 2, 3 or 4, Z is O, and $R^2$ is N or CH.

8. A compound according to claim 1, wherein X is pyrimidin-2-ylamino, pyridin-2-ylamino, imidazol-1-yl, imidazol-2-ylamino, benzimidazol-2-ylamino or 4,5-dihydroimidazol-2-ylamino, Y is —$(CH_2)_n$—, n is 2, 3 or 4, Z is O, $R^2$ is N or CH, and $R^4$ is phenyl which is unsubstituted or substituted by A, aryl or CF$_3$.

9. A compound according to claim 1, wherein X is pyrimidin-2-ylamino, pyridin-2-ylamino, imidazol-1-yl, imidazol-2-ylamino, benzimidazol-2-ylamino or 4,5-dihydroimidazol-2-ylamino, Y is —$(CH_2)_n$—, n is 2, 3 or 4, Z is O, $R^2$ is N or CH, and $R^4$ is phenyl which is unsubstituted or substituted by A, aryl or CF$_3$, and $R^5$ is OA or OH.

10. A compound according to claim 1, wherein X is pyrimidin-2-ylamino, pyridin-2-ylamino, imidazol-1-yl, imidazol-2-ylamino, benzimidazol-2-ylamino or 4,5-dihydroimidazol-2-ylamino, 2-aminoimidazol-5-ylamino, 2-aminopyridin-6-ylamino, 2-aminoimidazol-5-yl or 2-aminopyridin-6-yl, Y is —$(CH_2)_n$—, n is 2, 3 or 4, Z is O, $R^2$ is N or CH, and $R^4$ is unsubstituted phenyl, and $R^5$ is OA or OH.

11. A compound according to claim 1, wherein X is pyrimidin-2-ylamino, pyridin-2-ylamino, imidazol-1-yl, imidazol-2-ylamino, benzimidazol-2-ylamino or 4,5-dihydroimidazol-2-ylamino, Y is —$(CH_2)_n$—, n is 2, 3 or 4, Z is O, $R^2$ is N or CH, and $R^4$ is unsubstituted phenyl, and $R^5$ is OA or OH.

12. The pharmaceutical preparation according to claim 1, comprising at least one or more excipients, and/or assistants, and/or other active ingredients.

13. A method for combating illnesses based on expression and pathological function of $\alpha_v\beta_3$ integrin receptors comprising administering to a patient a therapeutically effective amount of a compound according to claim 1.

14. A method for combating pathological processes which are maintained or propagated by angiogenesis comprising administering to a patient a therapeutically effective amount of a compound according to claim 1.

15. The method according to claim 13, wherein the illness is thromboses, cardiac infraction, coronary heart diseases, arteriosclerosis, tumours, osteoporosis, fibroses, inflammation, infection, or psoriasis.

16. A method of influencing wound-healing processes comprising administering to a patient a therapeutically effective amount of a compound according to claim 1.

* * * * *